(12) United States Patent
El-Baz et al.

(10) Patent No.: US 10,667,778 B2
(45) Date of Patent: Jun. 2, 2020

(54) ACCURATE DETECTION AND ASSESSMENT OF RADIATION INDUCED LUNG INJURY BASED ON A COMPUTATIONAL MODEL AND COMPUTED TOMOGRAPHY IMAGING

(71) Applicant: University of Louisville Research Foundation, Inc., Louisville, KY (US)

(72) Inventors: Ayman S. El-Baz, Louisville, KY (US); Ahmed Soliman, Louisville, KY (US); Fahmi Khalifa, Louisville, KY (US); Ahmed Shaffie, Louisville, KY (US); Neal Dunlap, Louisville, KY (US); Brian Wang, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 20 days.

(21) Appl. No.: 15/704,719

(22) Filed: Sep. 14, 2017

(65) Prior Publication Data
US 2018/0070905 A1 Mar. 15, 2018

Related U.S. Application Data

(60) Provisional application No. 62/394,315, filed on Sep. 14, 2016.

(51) Int. Cl.
*A61B 6/00* (2006.01)
*G06T 7/33* (2017.01)
(Continued)

(52) U.S. Cl.
CPC ............ *A61B 6/5217* (2013.01); *A61B 6/032* (2013.01); *A61B 6/486* (2013.01); *A61B 6/50* (2013.01);
(Continued)

(58) Field of Classification Search
None
See application file for complete search history.

(56) References Cited

U.S. PATENT DOCUMENTS

| 10,470,734 | B2* | 11/2019 | Madabhushi | ............ G06T 7/136 |
| 2004/0101176 | A1* | 5/2004 | Mendonca | ............ G06T 7/0012 |
| | | | | 382/128 |
| 2008/0002870 | A1* | 1/2008 | Farag | ................... G06K 9/0014 |
| | | | | 382/128 |
| 2011/0243417 | A1* | 10/2011 | Madabhushi | ........ G06K 9/3233 |
| | | | | 382/131 |

(Continued)

OTHER PUBLICATIONS

Four-dimensional computed tomography pulmonary ventilation images vary with deformable image registration algorithms and metrics. (PMID:21520845) ; Yamamoto et al Mar. 1, 2011.*

(Continued)

*Primary Examiner* — Nancy Bitar
(74) *Attorney, Agent, or Firm* — Dentons Bingham Greenbaum Doll LLP; Brian W. Chellgren (57) ABSTRACT

A system and computation method is disclosed that identifies radiation-induced lung injury after radiation therapy using 4D computed tomography (CT) scans. After deformable image registration, the method segments lung fields, extracts functional and textural features, and classifies lung tissues. The deformable registration locally aligns consecutive phases of the respiratory cycle using gradient descent minimization of the conventional dissimilarity metric. Then an adaptive shape prior, a first-order intensity model, and a second-order lung tissues homogeneity descriptor are integrated to segment the lung fields. In addition to common lung functionality features, such as ventilation and elasticity, specific regional textural features are estimated by modeling the segmented images as samples of a novel $7^{th}$-order contrast-offset-invariant Markov-Gibbs random field (MGRF). Finally, a tissue classifier is applied to distinguish between the injured and normal lung tissues.

15 Claims, 10 Drawing Sheets
(10 of 10 Drawing Sheet(s) Filed in Color)

(51) Int. Cl.
*G06T 7/149* (2017.01)
*G06T 7/143* (2017.01)
*G06T 7/174* (2017.01)
*G06T 7/38* (2017.01)
*G06T 7/246* (2017.01)
*A61B 6/03* (2006.01)
*G06T 7/00* (2017.01)
*A61N 5/10* (2006.01)
*A61B 5/08* (2006.01)
*A61B 5/00* (2006.01)

(52) U.S. Cl.
CPC .......... *A61B 6/5235* (2013.01); *G06T 7/0016* (2013.01); *G06T 7/143* (2017.01); *G06T 7/149* (2017.01); *G06T 7/174* (2017.01); *G06T 7/246* (2017.01); *G06T 7/344* (2017.01); *G06T 7/38* (2017.01); *A61B 5/08* (2013.01); *A61B 5/7267* (2013.01); *A61B 2576/00* (2013.01); *A61N 5/1048* (2013.01); *G06T 2200/04* (2013.01); *G06T 2207/10076* (2013.01); *G06T 2207/10081* (2013.01); *G06T 2207/20076* (2013.01); *G06T 2207/20081* (2013.01); *G06T 2207/20084* (2013.01); *G06T 2207/30061* (2013.01)

(56) References Cited

U.S. PATENT DOCUMENTS

| | | | |
|---|---|---|---|
| 2012/0201445 A1* | 8/2012 | El-Baz | G06K 9/621 382/133 |
| 2013/0259345 A1* | 10/2013 | El-Baz | G06T 7/0012 382/131 |
| 2016/0113614 A1* | 4/2016 | Cetingul | G06T 11/006 382/131 |
| 2016/0260224 A1* | 9/2016 | Ward | G06T 7/0012 |
| 2017/0046839 A1* | 2/2017 | Paik | G06K 9/6296 |

OTHER PUBLICATIONS

Inverse 4D conformal planning for lung SBRT using particle swarm optimization to cite this article: A Modiri et al Jul. 2016 Phys. Med. Biol. 61 6181.*

Deformable image registration using convolutional neural networks Koen A.J. Eppenhof, Maxime W. Lafarge, Pim Moeskops, Mitko Veta, and Josien P.W. Pluim Medical Image Analysis Group (IMAGE/e), Department of Biomedical Engineering, Jul. 13, 2019.*

Four-dimensional computed tomography pulmonary ventilation images vary with deformable image registration algorithms and metrics Tokihiro Yamamotoa!; Mar. 2011.*

* cited by examiner

ACCURATE DETECTION AND ASSESSMENT OF RADIATION INDUCED LUNG INJURY BASED ON A COMPUTATIONAL MODEL AND COMPUTED TOMOGRAPHY IMAGING

CROSS REFERENCE TO RELATED APPLICATION

Pursuant to 37 C.F.R. § 1.78(a)(4), this application claims the benefit of and priority to prior filed Provisional Application Ser. No. 62/394,315, filed Sep. 14, 2018, which is expressly incorporated herein by reference in its entirety.

FIELD OF THE INVENTION

This disclosure generally relates to the detection and characterization of radiation induced lung injury associated with radiation therapy used to treat lung cancer.

BACKGROUND OF THE INVENTION

Radiation-induced lung injury is a significant side effect of radiation therapy for many lung cancer patients. Although higher radiation doses increase the radiation therapy effectiveness for tumor control, such higher doses may lead to lung injury because, under such conditions, a greater quantity of normal lung tissue may be included in treated areas. In recent studies, nearly 40% of patients who underwent radiation therapy developed lung injuries following treatment. Lung injury may take the form of acute radiation pneumonitis occurring less than six months after treatment, or lung injury may take the form of lung fibrosis, happening after six months of treatment. Conventional approaches to the detection and characterization of radiation-induced lung injury are expensive and rely on slow machines that produce images that have insufficient resolution.

Early detection may help to improve management of the treatment of radiation-induced lung injury. Conventional approaches that rely only on the appearance of computed tomography (CT) scans (i.e., Hounsfield Units) do not enable early detection of radiation-induced lung injury, making treatment more difficult. Alternatively, detection of early radiation-induced lung injury development through monitoring of lung functionality and lung texture changes may substantially improve the disease management. Although global pulmonary function tests (PFT), such as spirometry, measure air flow obstruction/restriction, no regional lung function information is obtained. Alternatively, the lung functionality may be locally evaluated using nuclear imaging, e.g., by single-photon emission computed tomography (SPECT) ventilation and perfusion (V/Q) images. However, SPECT image acquisition is highly expensive and relies on relatively slow machines, which produce images having insufficient spatial resolution.

Recently, four-dimensional computed tomography (4D-CT) scans have gained attention for assessing lung functionality in that such sans provide high spatial resolution, faster acquisition, and relatively low cost. Moreover, in addition to texture, many functional features may be derived from 4D-CT scans. The lung ventilation may be derived from the 4D-CT scans and these results may be correlated with the SPECT (V/Q) scans, or the ventilation maps may be correlated directly with certain clinical findings.

Despite limited success, however, conventional methods for detecting radiation therapy effects have several significant limitations. Global PFTs measure total airflow but fail to provide information about regional functionality. Nuclear imaging based detection of defects in local pulmonary function, for example, suffers from low spatial resolution. Conventional voxel-wise descriptors of lung appearance are too sensitive to noise and fail to take account of dependences between adjacent voxels to suppress noise impacts. Further, common computational models for aligning the 4D-CT images do not guarantee proper voxel-to-voxel matches, often leading to inaccurate estimates of lung functionality parameters.

SUMMARY OF THE INVENTION

A system and computation method is disclosed that overcomes problems associated with conventional approaches to the detection and characterization of radiation-induced lung injury after radiation therapy.

A system and method that accurately detects radiation induced lung injury is disclosed. The system includes at least one processor a memory coupled to the processor, the memory having computer program instructions stored thereon that, when executed by the processor, cause the processor to perform operations of the method. The method includes receiving a plurality of four-dimensional computed tomography (4D-CT) images from a corresponding plurality of lung configurations captured during different phases of an inhale/exhale process. The method further includes performing deformable image registration between various images of the plurality of 4D-CT images. The method also includes performing lung segmentation, extracting functional features from the 4D-CT images, and extracting textural features from the 4D-CT images. Further, the method includes identifying regions of radiation induced lung injury based on the computational model that is generated by the above-referenced method.

Further embodiments, features, and advantages, as well as the structure and operation of the various embodiments, are described in detail below with reference to the accompanying drawings.

BRIEF DESCRIPTION OF THE DRAWINGS

Embodiments are described with reference to the accompanying drawings. In the drawings, like reference numbers may indicate identical or functionally similar elements. The patent or application file contains at least one drawing executed in color. Copies of this patent or patent application publication with color drawing(s) will be provided by the Office upon request and payment of the necessary fee.

DETAILED DESCRIPTION

This document discloses a new and efficient computational framework to accurately align and segment lung regions from four-dimensional computed tomography (4D-CT) images, to extract discriminative features for early detection of radiation-induced lung injury, and to perform the detection.

Figure 1:
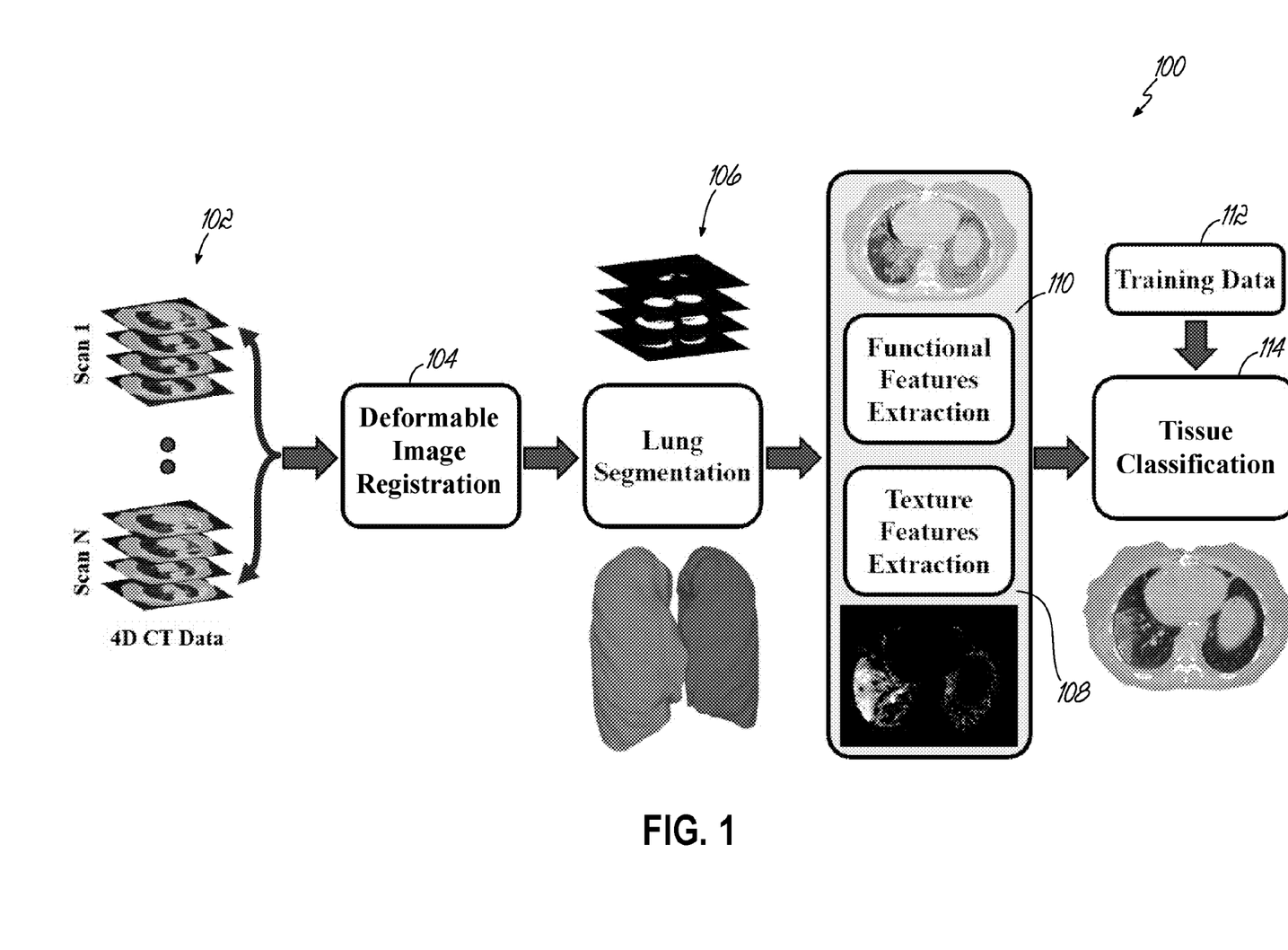
FIG. 1 is a schematic illustration of a computational framework 100 that performs efficient detection of radiation-induced lung injury, according to an embodiment.

FIG. 1 is a schematic illustration of a computational framework 100 that performs efficient detection radiation-induced lung injury, according to an embodiment. The disclosed framework 100, sequentially performs 102 deformable image registration (DIR) of four-dimensional (4D) lung computed tomography (CT) data received as input, performs 106 segmentation of the lung fields with a newly developed image model and methodology, extracts textural 108 and functional 110 features, and performs 114 tissue classification to detect the radiation-induced lung injury using a trainable classifier of lung tissues based on training data 112. The disclosed framework is described in greater detail below.

Lung Segmentation

Figure 2A:
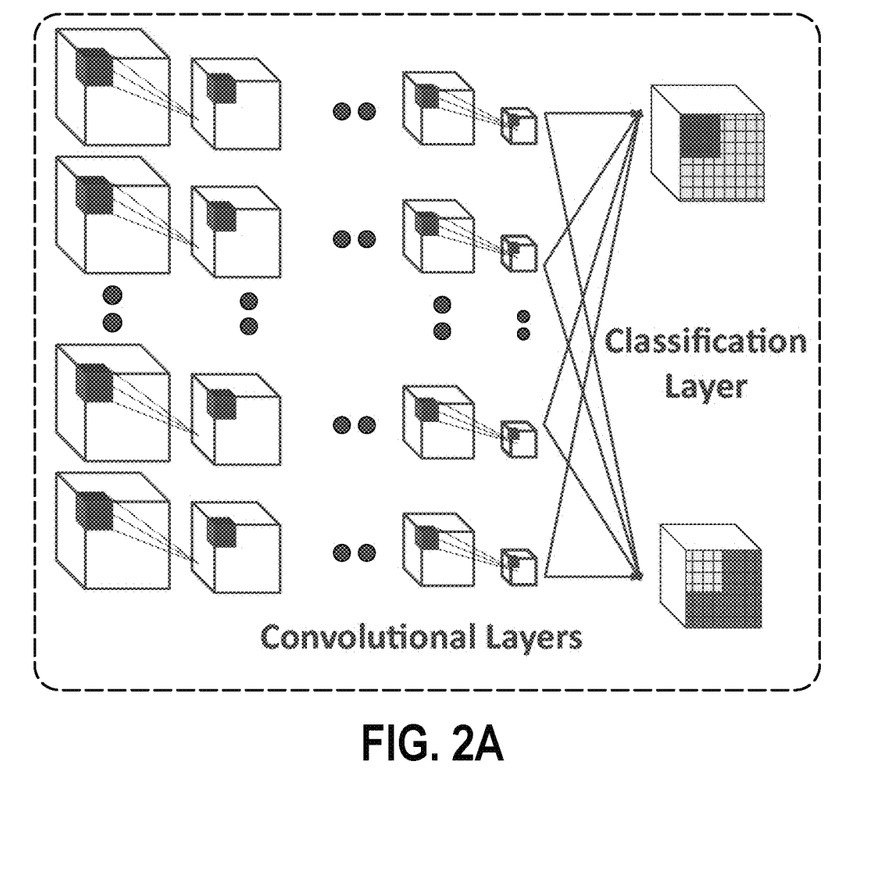
FIG. 2A is a schematic illustration of a computational method in which input image data is sequentially convolved with multiple filters at a plurality of cascaded network layers, according to an embodiment.

Image data of lung fields is segmented to ensure that all potentially injured regions will be examined. Determination of the lung fields in CT scans reduces inter-subject variations of estimated features, which is achieved by normalizing features inside lung fields in each data set by averaging over a corresponding chest region. Further, segmented lung masks at different respiratory phases are used for deformable image registration (DIR). Lung masks are further used as a volume of interest (VOI) for tissue classification analysis using a three-dimensional (3D) convolutional neural network (CNN) as illustrated in FIG. 2 and described in greater detail below. Accurate segmentation ensures accurate results at each step of the 3D CNN analysis.

Segmentation is performed using a framework that combines segmentations of a joint 3D Markov-Gibbs random field (MGRF) model of the original 3D scan with corresponding Gaussian-scale spaced-filtered volumes. The joint model integrates voxel-wise visual appearance features, pairwise spatial voxel interactions, and an adaptive shape prior of the lung that accounts for voxel location in addition to voxel intensity.

Disclosed embodiments enable segmentation of lung fields at different phases of the respiratory cycle, as follows. First, an exhale phase of the 4D data is segmented. Then, segmentation labels of the exhale volume are propagated to data corresponding to subsequent respiratory phases using only a modified adaptive shape prior component, which leads to an accurate and faster segmentation. Label propagation is based on visual appearance of CT images at different respiratory phases. A similar procedure may be applied to data corresponding to an inhale phase.

According to an embodiment, each voxel r of a different phase image t is mapped to the same location in an exhale lattice. Then, an initial search cube Cr of size cx:i×cy:i×cz:i is centered at the mapped location r for finding, in the cube Cr, all the exhale voxels with signal deviations within a predefined fixed range, k, from the mapped input signal, tr. If such voxels are absent in the exhale, the cube size is iteratively increased until the voxels within the predefined signal deviation range are found or a pre-defined final cube size is reached (preliminary experiments employed the following values: cx:i=cy:i=cz:i=3; λ from 50 to 125 with the step of Δλ=25, and the final cube size of cx:f=cy:f=cz:f=11).

Voxel-wise probabilities, Psh:r (k), k∈K, for the adaptive shape prior are then estimated based on determined voxels of similar appearance and corresponding voxel labels. A subset of similar voxels within the cube Cr in the exhale image is defined as Rr={φ:φ∈R; φ∈Cr; |g$_φ$−t$_r$|≤λ}. The cardinality (number of voxels) of this subset is denoted by Rr=card(Rr). Using these definitions, the final probability for each voxel may be calculated as:

$$P_{sh:r} = \frac{1}{R_r} \sum_{\varphi \in R_r} \delta(k - m_\varphi),$$

wherein δ(z) is the Kronecker delta-function: δ(0)=1 and 0 otherwise.

Deformable Image Registration

Accurate estimation of regional functional features is enabled by accurate spatial mapping between successive pairs of three-dimensional (3D) CT volumes of the respiratory cycle. Conventional 4D-CT registration methods seek to establish direct spatial correspondences between peak exhale and peak inhale images. However, such a registration leads to sizeable potential errors in corresponding displacement fields due to large changes in lung volumes between the two peak phases (i.e., between the peak inhale and peak exhale phases).

To reduce these errors that might greatly affect the estimated features, a sequential deformable image registration (DIR) 104 between successive 3D-CT volumes (i.e., segments of 4D lung CT data 102) of the respiratory cycle is performed. The registration establishes the voxel-wise displacement vector field, U={u(r)=$\Sigma_{i=1}^{N-1}$u$_i$(r): r∈$\mathbb{R}$}, which integrates displacements that exist between successive 3D-CT volumes 102. The total field, U, and its successive components, U$_i$={u$_i$(r):r∈$\mathbb{R}$}, defined on the initial 3D-CT volume $\mathbb{R}$, determine gradual changes of image geometry and reveals features along the cycle.

According to an embodiment, a non-rigid registration technique is used to determine the displacement fields. This is achieved using a two-step registration, which includes a global affine step of determining a calculated distance map for the segmented lungs followed by a local deformation of each voxel to its correspondence by solving the 3D Laplace equation, $$\nabla^2 \gamma = \frac{\partial^2 \gamma}{\partial x^2} + \frac{\partial^2 \gamma}{\partial y^2} + \frac{\partial^2 \gamma}{\partial z^2} = 0;$$

where γ(x, y, z) is an estimated "electric field" (i.e., not a physical electric field but a smooth function used to implement the deformation) between the reference and target surfaces, between each two corresponding iso-surfaces that generates streamlines from fixed volume voxels to displaced voxels.

The above-described algorithm for calculating the "electric field" is summarized as follows.

---

Algorithm1:- Estimating the electric field between two iso-surfaces to get the streamlines that maps different point to their correspondence.

1. Find the surface of both target and reference lung objects.
2. Initial condition: Set the maximum and minimum potential at the target surface and corresponding reference surface, respectively.
3. Estimate the electric field γ (Gradient of potential from source (high value), to destination (low value)) between both iso-surfaces using the following equation:

$$\gamma^{j+1}(x, y, z) = \frac{1}{6} \left\{ \begin{array}{c} \gamma^j(x + \Delta x, y, z) + \gamma^j(x - \Delta x, y, z) + \gamma^j(x, y + \Delta y, z) + \\ \gamma^j(x, y - \Delta y, z) + \gamma^j(x, y, z + \Delta z) + \\ \gamma^j(x, y, z - \Delta z) \end{array} \right\}$$

4. Iterate step 3 until convergence is achieved (i.e., there is no change in the estimated γ values between consequent iterations).

---

Then, a generalized Gaussian Markov random field (GGMRF) smoothing procedure is applied to the data to ensure anatomical consistency and best match according to Eq. 1, below:

$$\hat{p}_s = \arg \min_{\tilde{p}_s = (\tilde{x}_s^{ref}, \tilde{y}_s^{ref}, \tilde{z}_s^{ref})} \left\{ (|x_s^{ref} - \tilde{x}_s^{ref}|^\alpha + |y_s^{ref} - \tilde{y}_s^{ref}|^\alpha + |z_s^{ref} - \tilde{z}_s^{ref}|^\alpha) + \rho^\alpha \lambda^\beta \sum_{r \in N} \eta_{s,r} (|\tilde{x}_s^{ref} - x_r^{ref}|^\beta - |\tilde{y}_s^{ref} - y_r^{ref}|^\beta - |\tilde{z}_s^{ref} - z_r^{ref}|^\beta) + |q_s^{tar} - \tilde{q}_s^{ref}|^\alpha + \rho^\alpha \lambda^\beta \sum_{r \in N} \eta_{s,r} |\tilde{q}_s^{tar} - q_r^{ref}|^\beta \right\} \quad (1)$$

In Eq. 1, above, p$_s$=(x$_s^{ref}$, y$_s^{ref}$, z$_s^{ref}$) and p̃$_s$=(x̃$_s^{ref}$, ỹ$_s^{ref}$, z̃$_s^{ref}$) denote the initial 3D locations of the target voxels' correspondences and their expected estimates on the reference (i.e., the locations on the target lung and the reference lung used in the registration process, that is, one moving and the other fixed, respectively); q$_s^{tar}$ and q̃$_s^{ref}$ are the target voxel intensity and its estimate correspondences on the reference, respectively; N is the number of the nearest neighbor voxels; η$_{s,r}$ is the GGMRF potential, and ρ and λ are scaling factors. The level of smoothing is controlled by the β∈[1.01,2.0] parameter (e.g., β=1.01 for relatively abrupt vs. β=2 for smooth edges). The prior distribution of the estimator is determined by the α∈{1,2} parameter. Two specific values include α=2 (Gaussian) and α=1 (Laplace). In accordance with one embodiment of the invention, assessments were carried out based on the following specific parameter values: ρ=1, λ=5, β=1.01, α=2, and η$_{s,r}$=√2 for all directions. Other embodiments of the invention may be based on various other parameter values as used for the disclosed smoothing procedure.

Radiation-Induced Lung Injury Detection Using Texture and Functionality Features In accordance with embodiments of the invention, two categories of discriminative features are extracted using the segmented lung volumes and the calculated deformation fields. These features describe the lung alteration resulting from radiation therapy. Textural features 108 of the lungs may be modeled in terms of a Gibbs energy for the novel 7th-order contrast-offset-invariant 3D Markov-Gibbs random field (MGRF) image model (described in greater detail below), while functional features 110 of the lungs may be modeled using the Jacobian ventilation, describing the air flow in the lung, and functional strain describing the elasticity of the lung tissue. These feature categories are described in greater detail below.

The $7^{th}$-Order Textural Feature

Since the radiation therapy is generally concentrated around diseased lung regions, observed texture of affected tissue generally changes after the radiation therapy. To model changes in the visual appearance of the injured parts of the lung, the lung tissues are considered as samples of a trainable translation-offset and contrast-offset invariant $7^{th}$-order MGRF in accordance with one feature of the invention. The model relates the Gibbs probability of an image g=(g(r):r∈R) with the voxel-wise Hounsfield Units g(r) to a general-case $7^{th}$ order exponential family distribution:

$$P_7(g) = \frac{1}{Z}\psi(g)\exp(-E_7(g));$$

where ψ(g) is a core distribution, Z is the normalizing factor and $E_7$ (g) is the Gibbs energy of the image. In the invention, this model describes an image texture in terms of signal dependencies (interactions) between each voxel and its neighbors depending on how the training lungs have been affected.

This model accounts for partial ordinal interactions between voxel-wise signals in each particular voxel and within a radius p from a particular voxel for describing visual appearance of the radiation-induced lung injury in the CT scans. Given a training image g°, Gibbs potentials, $v_{7:\rho}$(g (r'): r'∈v(r)), of translation-invariant subsets of seven pixels to compute the energy $E_7$ (g) are learned using their approximate maximum likelihood estimates. The latter are obtained by generalizing the analytical approximation of potentials for a generic 2nd-order MGRF in:

$$v_{7:\rho}(\beta) = \frac{F_{7:\rho:core}(\beta) - F_{7:\rho}(\beta|g°)}{F_{7:\rho:core}(\beta)(1 - FF_{7:\rho:core}(\beta))}; \beta \in \mathbb{B}_7 \quad \text{Eq. (2)}$$

where β denotes a numerical code of a particular contrast-offset invariant relation between seven signals; $B_7$ is a set of these codes for all these 7-signal co-occurrences; $F_7$: ρ(g°) is an empirical marginal probability of the code β; β∈$B_7$, over all the 7-voxel configurations with the radius ρ in the image g°, and $F_{7:\rho:core}$(β) is the like probability for the core distribution.

Figure 2B:
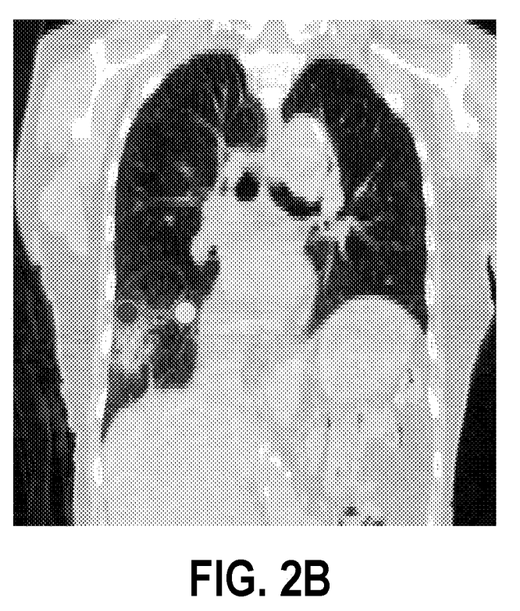
FIG. 2B is a schematic illustration of pairwise cliques, according to an embodiment.
Figure 2C:
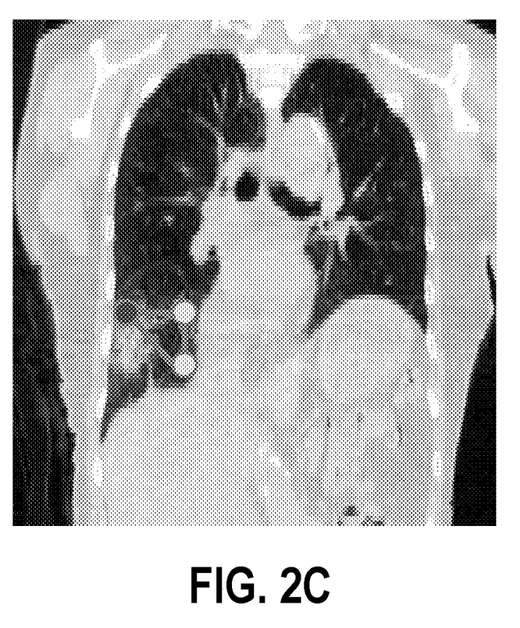
FIG. 2C is a schematic illustration of third-order cliques, according to an embodiment.

A clique is a subset of vertices of an undirected graph such that every two distinct vertices in the clique are adjacent. Cliques (C) represents the interaction between a certain voxel and its neighboring voxels. They are factored over an interaction graph, to quantify the probabilistic signal dependencies in the images. The interaction graph has nodes at the lattice sites (voxels) and edges, or arcs connecting interdependent or interacting pairs of the nodes. FIG. 2B provides an example of pairwise cliques and FIG. 2C shows an example of third order cliques.

The computed Gibbs energy monitors changes in the tissue signals over time and indicates the radiation-induced lung injury development, in accordance with an embodiment of the invention. The Gibbs energy is defined by $E_7(g)=\Sigma_{a=1}^{A}E_{7:a}(g)$, where $E_{7:a}(g)=\Sigma_{c_{a,v} \in C_a} V_{7:a}(g(\tilde{r}):\tilde{r} \in c_{a:r})$, $C_a$; a=1, ..., A, are K-order cliques, $c_{a,r} \in C_r$, of the same shape and size, energy. While a higher energy suggests a severe radiation effect, a lower Gibbs energy indicates a lower degree of radiation effect or injury. The appearance of radiation-induced lung injury and normal regions are quantified below by the voxel wise Gibbs energies for the three 7th-order translation- and contrast/offset-invariant MGRFs, each with a single family of fixed-shape central-symmetric voxel configurations v(r=(x, y, z))={(x, y, z); (x±ρ, y, z), (x, y±ρ, z), (x, y, z±ρ)}. Their potentials and distances, ρ, between the peripheral and central voxels are learned from g° by modifying the learning scenario described below. From a set of training data, a co-occurrence matrix for all possible cliques is calculated. For all possible cliques, the potentials using Eq. (2), and the Gibbs energy, $E_7$ (g), are then calculated and the energy is clustered into two classes (high energy and low energy). The high level is then selected and the low level energy is discarded.

The above-described algorithm for the MGRF modelling used in embodiments of the invention is summarized as follows.

---

Algorithm 2:- Learning the $7^{th}$-order MGRF appearance model.

1. Given a training CT g °, find the empirical injured (I = 1) and non-injured (I = 0) probability distributions, of the local ternary pattern (LTP)-based descriptors for different clique sizes r ∈ {1, ..., $r_{max}$} where the top size $r_{max}$ = 10 in our experiments.
2. Compute the empirical distributions of the same descriptors for the core Independent Random Field (IRF) ψ (g), e.g., for an image, sampled from the core.
3. Compute the approximate potentials' Maximum Likelihood Estimate (MLE), Eq. (2)
4. Compute partial Gibbs energies of the descriptors for equal and all other clique-wise signals over the training image for the clique sizes r = 1, 2, ..., 10 to choose the size$ρ_l$, such that both the energies are the closest one to another.

---

Figure 3A:
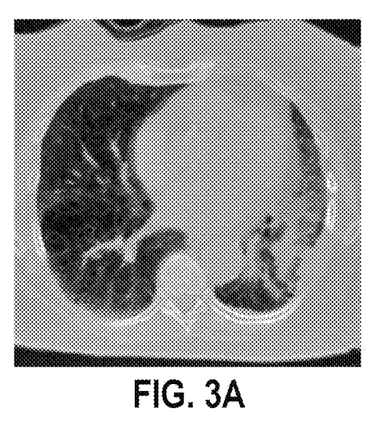
FIG. 3A illustrates a two-dimensional (2D) axial slice of image data, according to an embodiment.
Figure 3B:
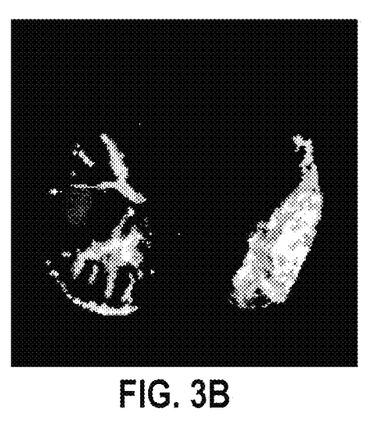
FIG. 3B illustrates a calculated 7th-order Gibbs energy corresponding to the image data of FIG. 3A, according to an embodiment.
Figure 3C:
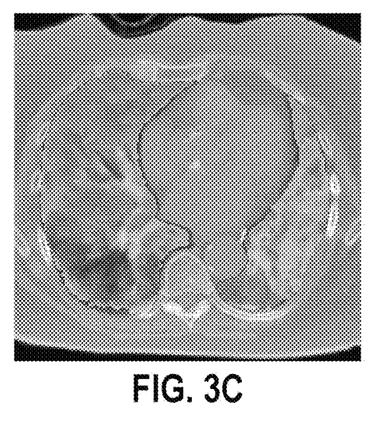
FIG. 3C illustrates a maximal strain feature corresponding to the image data of FIG. 3A, according to an embodiment.
Figure 3D:
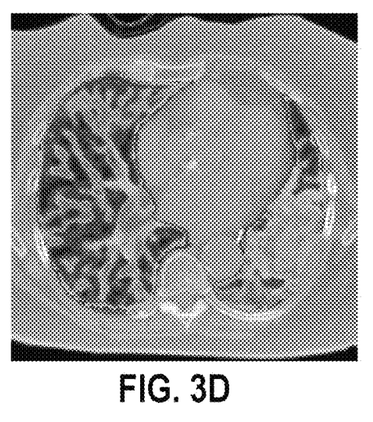
FIG. 3D illustrates a Jacobian ventilation corresponding to the image data of FIG. 3A, according to an embodiment.

FIG. 3A illustrates a two-dimensional (2D) axial slice of image data. FIG. 3B illustrates the corresponding calculated 7th-order Gibbs energy, in accordance with embodiments of the invention. As discussed below, functionality features of the lung are used and FIG. 3C presents the corresponding maximal strain feature, while FIG. 3D presents the corresponding Jacobian ventilation.

Functionality Feature Extraction

Functionality features are extracted from the calculated voxel-wise deformation fields obtained after registration of successive respiratory phases, the obtained voxel-wise deformation fields are used to calculate the following functionality features.

Functionality Strain

Functionality strain is used in embodiments of the invention for the identification of injured lung regions since the characteristics of injured regions change due to applied radiation therapy. The strain describes elasticity characteristics of the lung tissues. From the gradient of the displacement vector u(r), which maps the voxel at location r of the peak-exhale to its corresponding location in the peak-inhale image, the Lagrangian strain may be estimated mathematically as follows:

$$S = \begin{bmatrix} \frac{\partial u_x}{\partial x} & \frac{1}{2}\left(\frac{\partial u_x}{\partial y} + \frac{\partial u_y}{\partial x}\right) & \frac{1}{2}\left(\frac{\partial u_x}{\partial z} + \frac{\partial u_z}{\partial x}\right) \\ \frac{1}{2}\left(\frac{\partial u_y}{\partial x} + \frac{\partial u_x}{\partial y}\right) & \frac{\partial u_y}{\partial y} & \frac{1}{2}\left(\frac{\partial u_y}{\partial z} + \frac{\partial u_z}{\partial y}\right) \\ \frac{1}{2}\left(\frac{\partial u_z}{\partial x} + \frac{\partial u_x}{\partial z}\right) & \frac{1}{2}\left(\frac{\partial u_z}{\partial y} + \frac{\partial u_y}{\partial z}\right) & \frac{\partial u_z}{\partial z} \end{bmatrix} \quad (3)$$

In Eq. (3), the main diagonal components, $$\frac{\partial u_x}{\partial x}, \frac{\partial u_y}{\partial y}, \text{ and } \frac{\partial u_z}{\partial z}$$

define the linear strain along x, y, and z respectively. The shear strain components are calculated using off-diagonal components as $$\gamma_{i,j} = \frac{1}{2}\left(\frac{\partial u_i}{\partial j} + \frac{\partial u_j}{\partial i}\right) = \gamma_{j,i}; i, j \in \{x, y, z\}, i \neq j).$$

In terms of u(r), the strain tensor can be expressed as $S = \frac{1}{2}[\nabla u + (\nabla u)^T]$, where:

$$\nabla u(r) = \begin{bmatrix} \frac{\partial u_x}{\partial x} & \frac{\partial u_x}{\partial y} & \frac{\partial u_x}{\partial z} \\ \frac{\partial u_y}{\partial x} & \frac{\partial u_y}{\partial y} & \frac{\partial u_y}{\partial z} \\ \frac{\partial u_z}{\partial x} & \frac{\partial u_z}{\partial y} & \frac{\partial u_z}{\partial z} \end{bmatrix}. \quad (4)$$

Jacobian Ventilation

The Jacobian ventilation, which measures a partial volume change resulting from airflow during inspiration, is a good indicator to estimate regional ventilation, in accordance with embodiments of the invention. The voxel-wise volume at the inhale phase is estimated as $V_{in}^r = V_{ex}^r J_r$ and the exhale-to-inhale volume change is given by $\Delta V_r = V_{in}^r - V_{ex}^r = V_{ex}^r(J_r - 1)$ where $J_r$ is the voxel-wise Jacobian determinant that is also estimated from the gradient of the displacement fields as $J_r = |\nabla' u(r) + I|$, where $\nabla u(r)$ is the gradient of u(r) for each voxel, and I is the identity matrix, and $\nabla u(r)$ is the gradient of u(r) for each voxel in Eq. (3).

Tissue Classification

To detect and segment the injured tissues, in accordance with embodiments of the invention, the determined and estimated features and data are used together as input to a convolutional neural network (CNN) to generate tissue classifications. Specifically, all the estimated features ($E_7$ (g), $\Delta VJ$, and the maximum eigenvalue of the strain matrix of Eq. (3)), in addition to the raw exhale phase (shown in FIGS. 3A-3D) are used as 3D input volumes to the deep convolutional neural network. The CNN learns discriminative characteristics from the different 3D data inputs by using the training database that contains data for both injured and normal lungs. In one embodiment, a deep 3D CNN is used for the generation of soft segmentation maps followed by a fully-connected 3D conditional random field (CRF) to produce the final labeled output of the segmented injuries. In this regard, each voxel of the data is assigned a probability value indicating the probability that the particular voxel corresponds to a region of injured tissue. The higher probability of injury is assigned the value of 1 in the final segmentation and the lower probability is assigned a value of 0.

The input is sequentially convolved with multiple filters at the cascaded network layers as illustrated schematically in FIG. 2A. The CNN consists of multiple layers (seven, in experiments according to an embodiment). Each layer takes input volumes and performs a convolution operation between the input volumes and kernels of predefined size ($5^3$, in experiments according to an embodiment), the inputs to the first layers are the data of the calculated features (Functionality and appearance), and its outputs are feature maps (FMs) that try to extract the discriminative patterns. These FMs are the inputs to the second layer that performs the same operations as the first layer to extract different FMs, and so on until the last layer, which is a fully connected layer that classifies the final output.

The architecture of the used CNN consists of seven layers with kernels of size $5^3$ (as described above), the receptive field (input voxel neighborhood influencing the activation of a neuron) size is $17^3$. The kernels for the classification layer is $1^3$. The advantage of this architecture, in the invention, is its ability to capture 3D contextual information from the provided feature volumes.

In further embodiment, radiation induced lung injury may be classified using a trainable random forest (RF) classifier of lung tissues.

Experimental Results and Conclusions

The disclosed methods have been testing in detailed studies based on 4D-CT data from 13 lung cancer patients that were scheduled to receive radiation therapy. The 4D-CT data was collected using a Philips Brilliance Big Bore CT scanner with a Varian real-time position management (RPM) system (Varian Medical Systems, Palo Alto, Calif.) for respiratory traces. The data spacing for the collected data ranges from 1.17×1.17×2.0 mm to 1.37×1.37×3.0 mm. To obtain functionality and appearance features for training a deep CNN network, the CT data were contoured by a radiologist. Then the deep network was applied to the voxels within the VOI determined by the segmented lung mask in a "leave-one-subject-out scenario." The voxels were classified as normal or injured tissue, and morphological operations were used for refinement, removal of scattered voxels, and hole filling.

3D feature values and raw exhale volume (i.e., corresponding Hounsfield Units values) inside the VOI are normalized to have zero mean and unity standard deviation to accelerate the convergence by reducing an internal covariant shift. FIGS. 4A-4F show a two-dimensional (2D) illustration of the 4D-CT segmentation that propagates labels of the exhale phase to the inhale phase along the image that shows the overlap between the two phase images before and after the DIR registration.

Figure 4A:
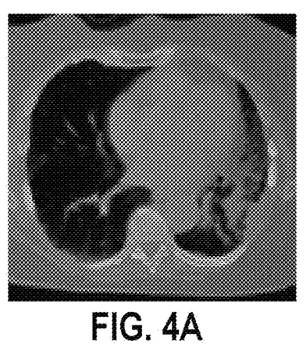
FIG. 4A shows a 2D axial slice of image data for an exhale phase, according to an embodiment.
Figure 4B:
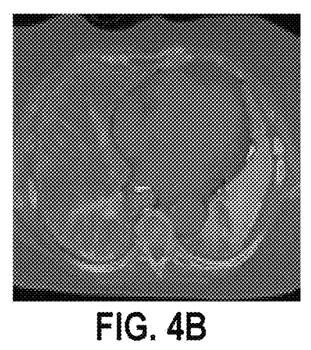
FIG. 4B shows segmentation of the exhale data of FIG. 4A, according to an embodiment.
Figure 4C:
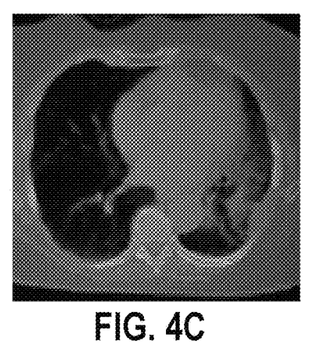
FIG. 4C shows overlap of image data from FIGS. 4A and 4B after registration, according to an embodiment.
Figure 4D:
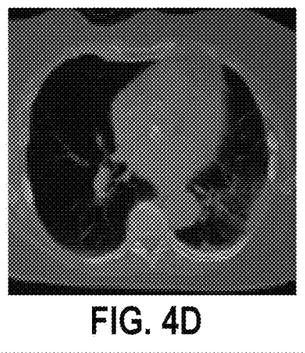
FIG. 4D shows a 2D axial slice of image data for the inhale phase of FIG. 4A.
Figure 4E:
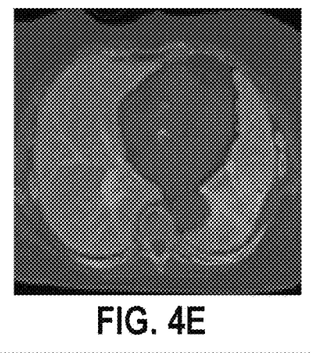
FIG. 4E shows segmentation of the inhale data of FIG. 4D, according to an embodiment.
Figure 4F:
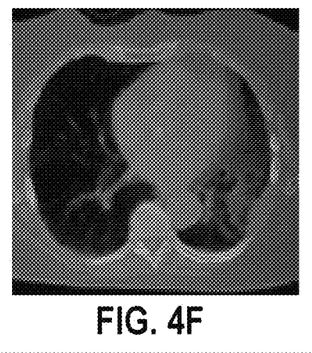
FIG. 4F shows overlap of image data from FIGS. 4A and 4B before registration, according to an embodiment.

FIGS. 4A-4F show typical two axial slices at the same cross section for exhale phase (FIG. 4A) with its segmentation (FIG. 4B), and inhale phase (FIG. 4D) with its segmentation (FIG. 4E)—their overlap before the registration (FIG. 4F) and after the registration (FIG. 4C). The color codes are: green for true positive, yellow for false positive, magenta for false negative, and red for ground truth edges.

Average lung segmentation accuracy, as quantified by a Dice similarity coefficient (DSC) which characterizes spatial overlap, was determined to be 99% with average execution time of 7.3 sec, while the DIR accuracy in terms of target registration error (TRE) equals 1.37±1.03 mm. The TRE is defined to be the average distance in mm, between multiple land marks in the lungs before and after the registration The performance of the deep network tested on the measured datasets has been evaluated in terms of accuracy Acc, sensitivity Sens, and specificity Spec, defined as $$Acc = \frac{TP + TN}{TP + TN + FP + FN}, Sens = \frac{TP}{TP + FN}, Spec = \frac{TN}{TN + FP},$$

where TP, TN, FP, and FN are the number of true positive, true negative, false positive, and false negative respectively.

The performance measures are listed in Table 1, below, for different feature group (FG), using only the raw exhale phase (FG1), exhale phase in addition to functionality features (FG2), in addition to texture features (FG3). Clearly, combining features improves accuracy because these features appear to complement each other in both early and late stages of lung injury.

TABLE 1

Performance Metrics

| | Classification Metrics | | | Segmentation Metrics | | |
|---|---|---|---|---|---|---|
| | AUC | Acc | Sens | Spec | Dice | BHD | AVD |
| FG1 | 94.1 | 91.8 | 79.1 | 96.3 | 72.7 | 19.4 | 9.5 |
| FG2 | 96.3 | 92.6 | 81.0 | 96.5 | 82.9 | 14.2 | 6.0 |
| FG3 | 99.0 | 95.4 | 86.8 | 98.3 | 88.0 | 5.2 | 4.6 |

The results presented in Table 1 are based on the following data: FG1 (4D-CT volume), FG2 (4D-CT volume and functionality features), and FG3 (4D-CT volume, functionality, and appearance features).

Classification accuracy has been evaluated using the area under the curve (AUC) for different feature groups. The AUC for using the FG1 only equals 0.94, while for the FG2 equals 0.96. When combining all the features in the classification process, the AUC has increased to 0.99. This enhancement highlights the advantages of integrating both the texture and functionality features as discriminatory ones for the detection of radiation-induced lung injury.

In addition to the Dice similarity coefficient, the segmentation accuracy for the injured tissues has been evaluated for each subject with bidirectional Hausdorff distance (BHD), and percentage volume difference (PVD) [24, 25], which characterize maximum surface-to-surface distances, and volume differences, respectively, between the segmented and "ground-truth" injured regions. Table 1 summarizes the Dice similarity coefficient, BHD, and PVD statistics for all test subjects showing the effect of different FG of our framework. The ground truth borders were outlined manually by a radiologist. The mean±standard deviation of the Dice similarity coefficient, BHD, and PVD for all the test subjects using our proposed framework is 88.0±3.5%, 5.2±1.3 mm, and 4.6±0.7%, respectively. FIG. 4 shows sample radiation-induced lung injury segmentation using different FGs.

Figure 5A:
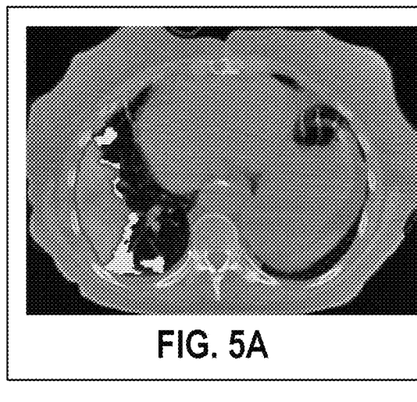
FIG. 5A illustrates a typical 2D segmentation for one axial slice using FG1 features (4D-CT volume), according to an embodiment.
Figure 5B:
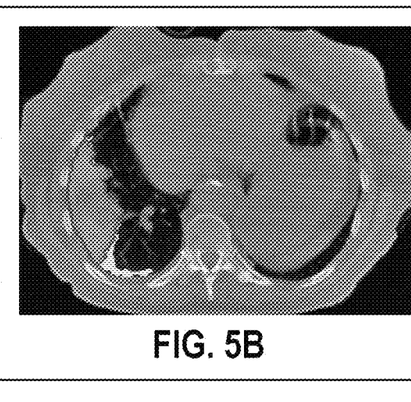
FIG. 5B illustrates a typical 2D segmentation for one axial slice using FG2 features (4D-CT volume and functionality features), according to an embodiment.
Figure 5C:
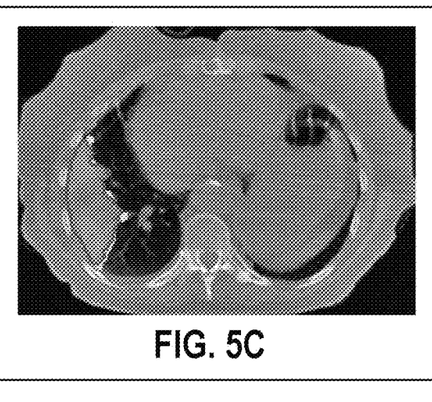
FIG. 5C illustrates a typical 2D segmentation for one axial slice using FG3 features (4D-CT volume, functionality, and appearance features), according to an embodiment.
Figure 6A:
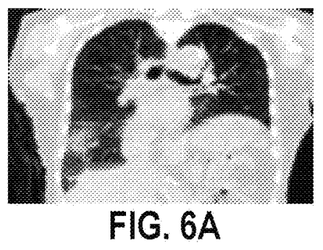
FIG. 6A illustrates 4D-CT image data corresponding to a peak inhale lung configuration, according to an embodiment
Figure 6B:
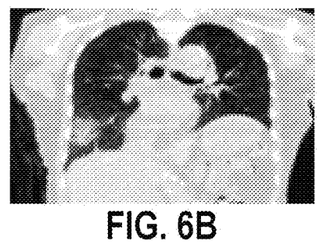
FIG. 6B illustrates 4D-CT image data corresponding to a peak exhale lung configuration, according to an embodiment
Figure 6C:
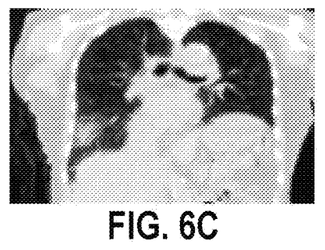
FIG. 6C illustrates a deformed inhale image, according to an embodiment.
Figure 6D:
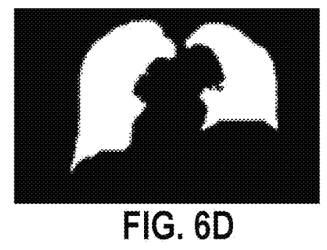
FIG. 6D illustrates lung segmentation based on a computational model, according to an embodiment.
Figure 6E:
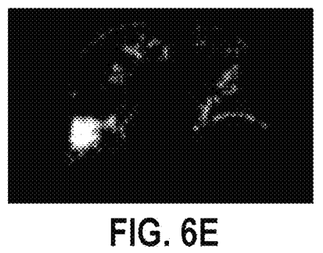
FIG. 6E illustrates voxel-wise 7th-order Gibbs energies, according to an embodiment.
Figure 6F:
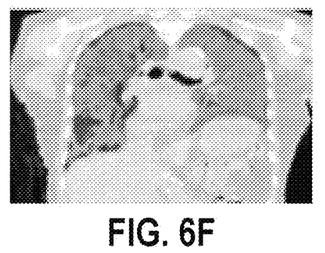
FIG. 6F illustrates color-coded estimated Jacobian ventilation, according to an embodiment.
Figure 6G:
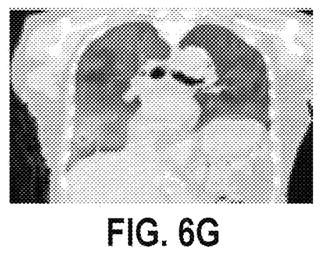
FIG. 6G illustrates a maximal lung strain component, according to an embodiment.
Figure 6H:
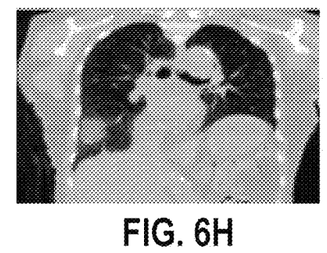
FIG. 6H illustrates classified injured lung regions, according to an embodiment.
Figure 7A:
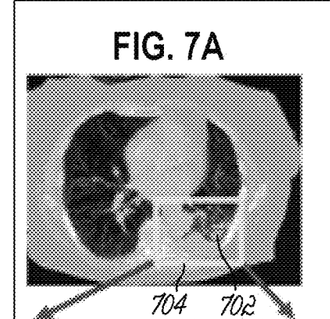
FIG. 7A illustrates injured regions from a first subject, projected onto the axial plane for visualization, according to an embodiment.
Figure 7B:
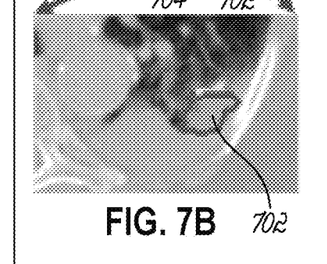
FIG. 7B illustrates an enlarged view of injured regions from FIG. 7A, projected onto the axial plane for visualization, according to an embodiment.
Figure 7C:
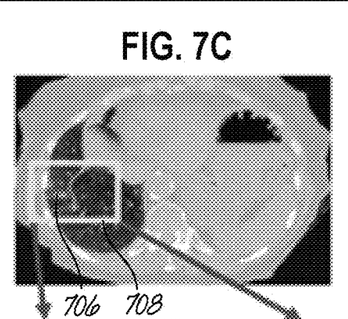
FIG. 7C illustrates injured regions from a second subject, projected onto the axial plane for visualization, according to an embodiment.
Figure 7D:
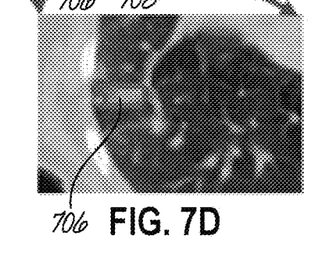
FIG. 7D illustrates an enlarged view of injured regions from FIG. 7C, projected onto the axial plane for visualization, according to an embodiment.
Figure 7E:
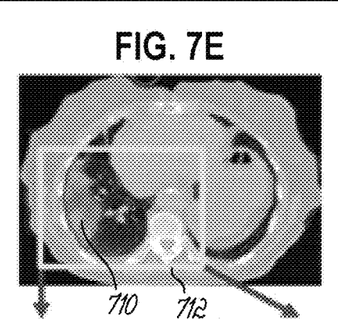
FIG. 7E illustrates injured regions from a third subject, projected onto the axial plane for visualization, according to an embodiment.
Figure 7F:
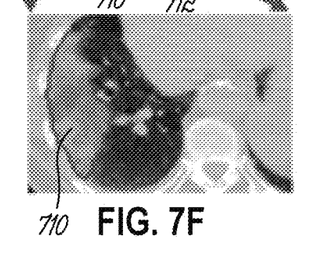
FIG. 7F illustrates an enlarged view of injured regions from FIG. 7E, projected onto the axial plane for visualization, according to an embodiment.
Figure 7G:
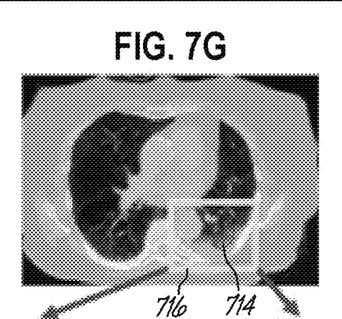
FIG. 7G illustrates injured regions from a fourth subject, projected onto the axial plane for visualization, according to an embodiment.
Figure 7H:
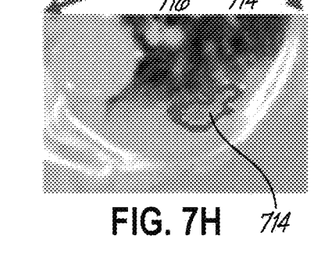
FIG. 7H illustrates an enlarged view of injured regions from FIG. 7G, projected onto the axial plane for visualization, according to an embodiment.

FIGS. 5A-5C illustrate typical 2D segmentation for one axial slice using FG1 features (in FIG. 5A), using FG2 features (in FIG. 5B), and using FG3 features (in FIG. 5C). The color codes are green for true positive, yellow for false positive, magenta for false negative, and red for ground truth.

According to further embodiments, FIGS. 6A-6H illustrate processing steps for one subject to show that the disclosed computational framework correctly identifies the injured lung region and demonstrates strong correlation between the estimated textural and ventilation features. Since the radiation-induced lung injury affects the lung regions, the accuracy of the computational framework was evaluated with the area-based Dice similarity coefficient, which characterizes agreement between the identified and true regions. Although the method is fully automated, test cases were compared with a ground truth estimate to verify accuracy. In these examples, the ground truth estimates are regions that were identified by a radiologist as injured regions.

Further identified injured regions from different subjects, projected onto different planes for visualization, are presented in FIGS. 7 and 8. For example, FIG. 7A illustrates injured regions 702 from a first subject, projected onto the axial plane for visualization, according to an embodiment. FIG. 7B presents an enlarged view of the inset 704 of FIG. 7A showing the identified injured region 702 in greater detail. Similarly, FIG. 7C illustrates injured regions 706 from a second subject, projected onto the axial plane for visualization, while FIG. 7D presents an enlarged view of the inset 708 of FIG. 7C showing the identified injured region 706 in greater detail. FIG. 7E illustrates injured regions 710 from a third subject, projected onto the axial plane for visualization, while FIG. 7F presents an enlarged view of the inset 712 of FIG. 7E showing the identified injured region 710 in greater detail. FIG. 7G illustrates injured regions 714 from a fourth subject, projected onto the axial plane for visualization, while FIG. 7H presents an enlarged view of the inset 716 of FIG. 7G showing the identified injured region 714 in greater detail.

Figures 8A, 8B:
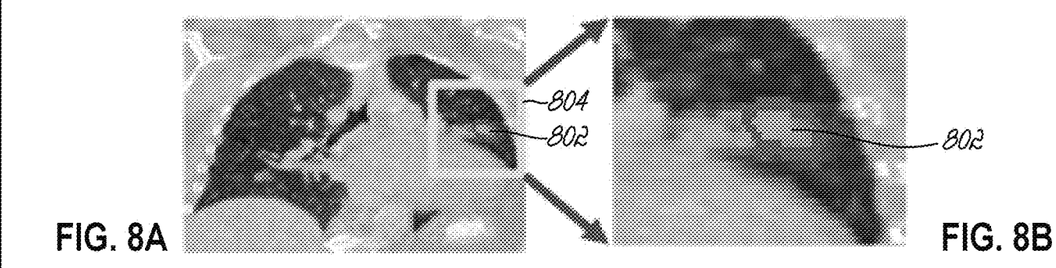
FIG. 8A illustrates injured regions from a first subject, projected onto the coronal plane for visualization, according to an embodiment.
FIG. 8B illustrates an enlarged view of injured regions from FIG. 8A, projected onto the coronal plane for visualization, according to an embodiment.
Figures 8C, 8D:
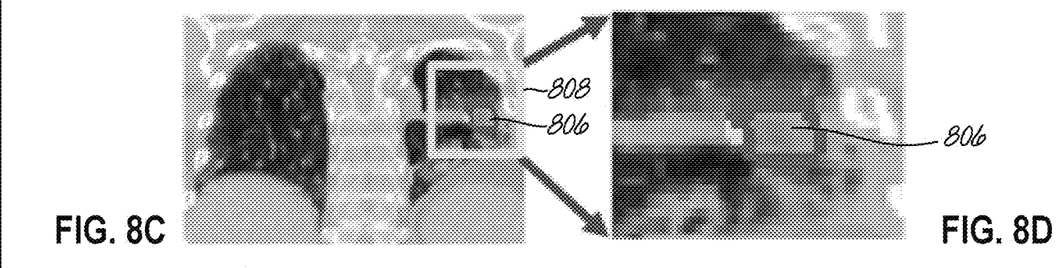
FIG. 8C illustrates injured regions from a second subject, projected onto the coronal plane for visualization, according to an embodiment.
FIG. 8D illustrates an enlarged view of injured regions from FIG. 8C, projected onto the coronal plane for visualization, according to an embodiment.
Figures 8E, 8F:
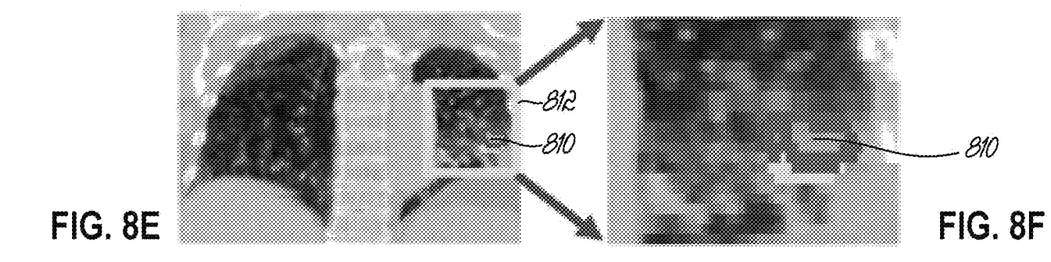
FIG. 8E illustrates injured regions from a third subject, projected onto the coronal plane for visualization, according to an embodiment.
FIG. 8F illustrates an enlarged view of injured regions from FIG. 8E, projected onto the coronal plane for visualization, according to an embodiment.

FIG. 8A illustrates injured regions 802 from a first subject, projected onto the coronal plane for visualization, according to an embodiment. FIG. 8B presents an enlarged view of the inset 804 of FIG. 8A showing the identified injured region 802 in greater detail. Similarly, FIG. 8C illustrates injured regions 806 from a second subject, projected onto the coronal plane for visualization, while FIG. 8D presents an enlarged view of the inset 808 of FIG. 8C showing the identified injured region 806 in greater detail. FIG. 8E illustrates injured regions 810 from a third subject, projected onto the coronal plane for visualization, while FIG. 8F presents an enlarged view of the inset 812 of FIG. 8E showing the identified injured region 810 in greater detail.

The mean standard deviation of the Dice similarity coefficient for all the test subjects in FIGS. 6A-6H, 7A-7H, and 8A-8F, is 0.87±0.08. The classification accuracy was evaluated by using the receiver operating characteristic (ROC), which tests sensitivity of the framework against the selected operating points (classification thresholds).

Figure 9:
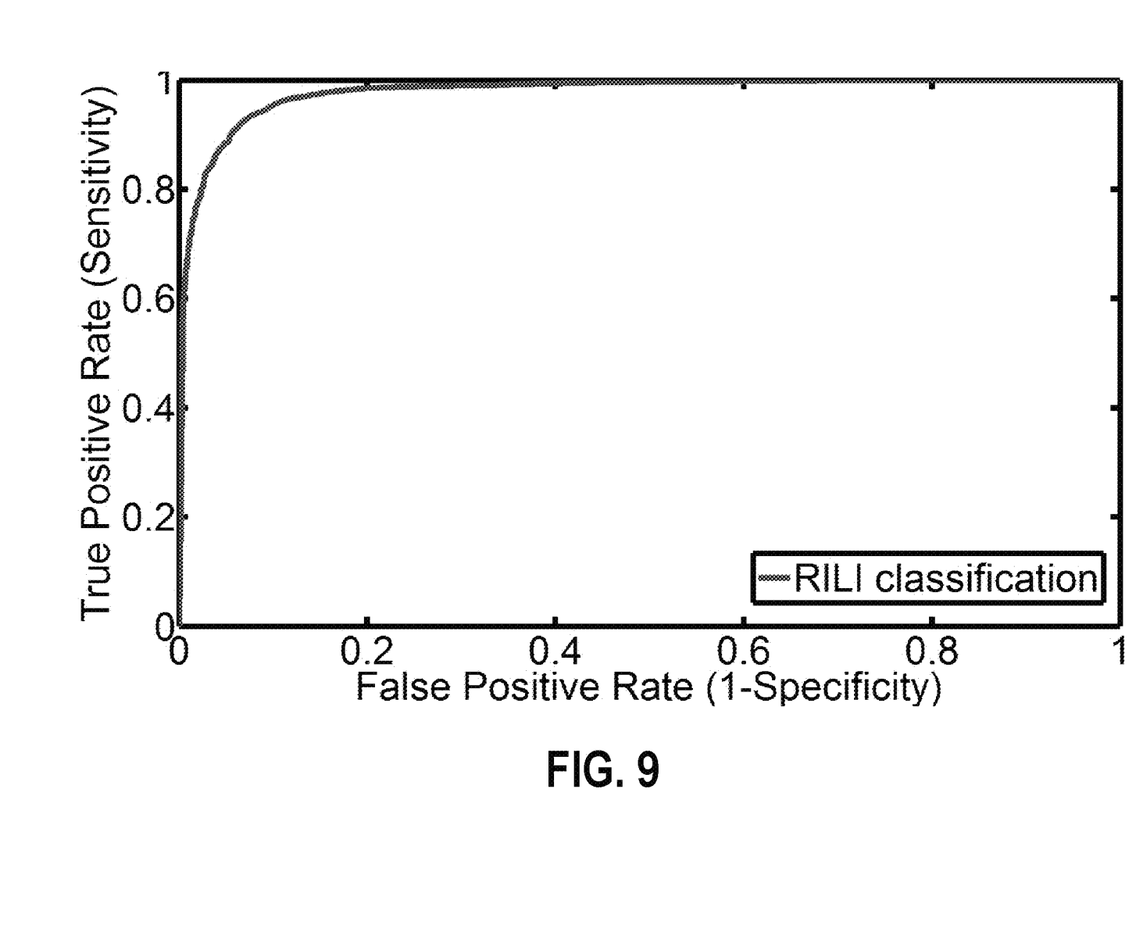
FIG. 9 demonstrates that the disclosed framework has very good performance, evidenced by the area of 0.962 under the ROC curve, according to an embodiment.

FIG. 9 demonstrates that the disclosed framework has very good performance, evidenced by the area of 0.962 under the ROC curve, according to an embodiment.

This disclosure introduced a processing pipeline for the detection of radiation-induced lung injury using 4D-CT lung data. The pipeline consists of 4D-CT lung segmentation, deformable image registration, extraction of discriminative feature, and injured tissue segmentation using 3D CNN. The segmentation/detection results based on a set of 13 patients who underwent the radiation therapy confirm that the proposed framework holds promise for early detection for lung injury.

What is claimed is:

1. A system that accurately detects radiation induced lung injury, comprising:
at least one processor; and
a memory coupled to the processor, the memory having computer program instructions stored thereon that, when executed by the processor, cause the processor to perform the following operations:
receiving a plurality of 4D-CT images from a corresponding plurality of lung configurations captured during different phases of an inhale/exhale process, including images captured during phases of the inhale/exhale process apart from peak inhale and peak exhale;
performing deformable image registration between various images of the plurality of 4D-CT images; performing lung segmentation;
extracting functional features from the 4D-CT images, wherein the functional features include a functional strain field and ventilation;
extracting textural features from the 4D-CT images, wherein textural features are identified based on a 7th order contrast offset Markov-Gibbs random field; and
comparing extracted functional features and textural features using a convolutional neural network to determine regions of normal tissue and radiation induced injured lung tissue.

2. The system of claim 1, wherein lung segmentation is based on a joint 3D Markov-Gibbs random field.

3. The system of claim 1, wherein the deformable image registration is a sequential deformable image registration between successive 3D-CT volumes that establishes a voxel-wise displacement vector field.

4. The system of claim 3, wherein the voxel-wise displacement vector field is estimated by numerical minimization of a regularized registration error measured by a sum of squared differences.

5. The system of claim 1, wherein lung segmentation is performed by analysis of both voxel location and voxel intensity.

6. The system of claim 1, wherein lung segmentation is performed using a shape prior that is constructed from a database of training 4D-CT images.

7. The system of claim 1, wherein identifying regions of radiation induced lung injury.

8. The system of claim 1, wherein textural features are determined based on signal dependencies between each voxel and its neighbors.

9. The system of claim 1, wherein each voxel is identified by the convoluted neural network as corresponding to healthy or injured lung tissue.

10. The system of claim 1, wherein identifying regions of radiation induced lung injury is based on features of a computed functional strain field.

11. The system of claim 1, wherein identifying regions of radiation induced lung injury is based on a Jacobian ventilation that comprises a voxel-wise Jacobian determinant.

12. A processor-implemented method of accurately detecting radiation induced lung injury, comprising:
receiving, by a processor, a plurality of 4D-CT images from a corresponding plurality of lung configurations captured during different phases of an inhale/exhale;
process, including images captured during phases of the inhale/exhale process apart from peak inhale and peak exhale;
performing, by the processor, deformable image registration between various images of the plurality of 4D-CT images; performing lung segmentation;
extracting functional features from the 4D-CT images;
determining functional features by computing a functional strain field and ventilation;
extracting textural features from the 4D-CT images;
computing a 7th order contrast offset Markov-Gibbs random field;
identifying textural features based on the 7th order contrast offset Markov-Gibbs random field;
and identifying, using a convolutional neural network, regions of radiation induced lung injury and regions of normal tissue based at least in part on the functional features and the textural features.

13. The method of claim 12, further comprising:
performing lung segmentation by computing a joint 3D Markov-Gibbs random field.

14. The method of claim 12, further comprising:
establishing a voxel-wise displacement vector field by determining a sequential deformable image registration between successive 3D-CT volumes.

15. The method of claim 14, further comprising:
performing a numerical minimization of a regularized registration error measured by a sum of squared differences to estimate the voxel-wise displacement vector field.

* * * * *